United States Patent
McDonald et al.

[11] Patent Number: 5,947,122
[45] Date of Patent: Sep. 7, 1999

[54] FLUID COLLECTION DRAPE

[75] Inventors: David McDonald, Norton, Mass.; Stephen A. Bollinger, Tucson, Ariz.; John T. Garibotto, Palo Alto, Calif.

[73] Assignee: Mentor Corporation, Santa Barbara, Calif.

[21] Appl. No.: 09/008,223

[22] Filed: Jan. 16, 1998

[51] Int. Cl.[6] .................................................. A61B 19/00
[52] U.S. Cl. ............................................................ 128/849
[58] Field of Search ................................... 128/849–856

[56] References Cited

U.S. PATENT DOCUMENTS

| | | | |
|---|---|---|---|
| 3,668,050 | 6/1972 | Donnelly | 128/853 |
| 5,151,314 | 9/1992 | Brown | 128/849 |
| 5,161,544 | 11/1992 | Morris | 128/853 |
| 5,174,306 | 12/1992 | Marshall | 128/852 |

*Primary Examiner*—Michael A. Brown
*Attorney, Agent, or Firm*—Fish & Richardson, P.C.

[57] ABSTRACT

A fluid collection drape for use during surgery includes an impermeable liner, a permeable facing, and a substrate sandwiched between the impermeable liner and the permeable facing. The fluid collection drape is provided in a sterile condition and is sized at about 3 feet by 2.5 feet to substantially cover a width of an operating table. The substrate absorbs greater than about 500 cc of fluid. The fluid collection drape is stored in a sterile state within a package. The substrate has a thickness of about 0.05 inch.

18 Claims, 2 Drawing Sheets

FLUID COLLECTION DRAPE

BACKGROUND OF THE INVENTION

This invention relates to a fluid collection drape for use during surgery.

Often during surgical procedures large amounts of fluids are present. Some fluids are introduced into a patient's body, for example, to inject medication. Other fluids become part of the surgical environment as a result of the surgical procedure, for example, bodily fluids.

Ultrasonically assisted lipoplasty (UAL) is a type of surgery in which unwanted fatty deposits are removed. A probe is inserted through a number of incisions made in the patient's skin to treat regions of fatty deposits. Fluid is routinely injected through the incisions during UAL.

During UAL, the injected fluids and other bodily fluids seep out of the incision sites, especially when the patient is repositioned. These fluids contaminate the operating area, increasing the probability of infection, cross-contamination, and spread of disease.

SUMMARY OF THE INVENTION

In general, the invention features a fluid collection drape for use during surgery. The collection drape includes an impermeable liner, a permeable facing, and a substrate sandwiched between the impermeable liner and the permeable facing. The fluid collection drape is provided in a sterile condition and is sized to substantially cover a width of a surgical operating table.

Preferred embodiments may include one or more of the following features. The fluid collection drape is stored in a sterile state within a package. The fluid collection drape is constructed to be sterilizable by application of gamma radiation, ethylene oxide, steam sterilizing, or dry heat. The substrate is configured to absorb greater than about 500 cc of a fluid. The substrate is configured to absorb about 100 cc of fluid per square foot. The permeable facing is attached to the impermeable lining along their perimeters by, e.g., a hot melt adhesive. The fluid collection drape is about 3.0 feet by 2.5 feet. The thickness of the substrate is about 0.05 inch. The lining is made of polypropylene, and the facing is a spunbond non-woven polypropylene. The substrate includes a super absorbent polymer.

According to another aspect of the invention, a method of defining a sterile operating environment during surgery includes placing a sterile drape on the operating table. The sterile drape includes a highly absorbent material having a thickness of about 0.05 inch and which is capable of absorbing greater than about 500 cc of fluid. During surgery, fluid is absorbed by the sterile drape.

Preferred embodiments may include the surgery being lipoplasty, e.g., ultrasonically assisted lipoplasty.

Among the advantages of the invention are that the fluid collection drape is highly absorbent, sterile, and sized to collect fluid from all areas of the operating region on the surgical operating table. The fluid collection drape prevents fluid from dripping on the floor, enhances safety (e.g., by reducing slippery surfaces), and reduces risk of cross contamination, spread of disease, and infection.

Other features and advantages of the invention will be apparent from the following detailed description and from the claims.

DETAILED DESCRIPTION

Figure 1:
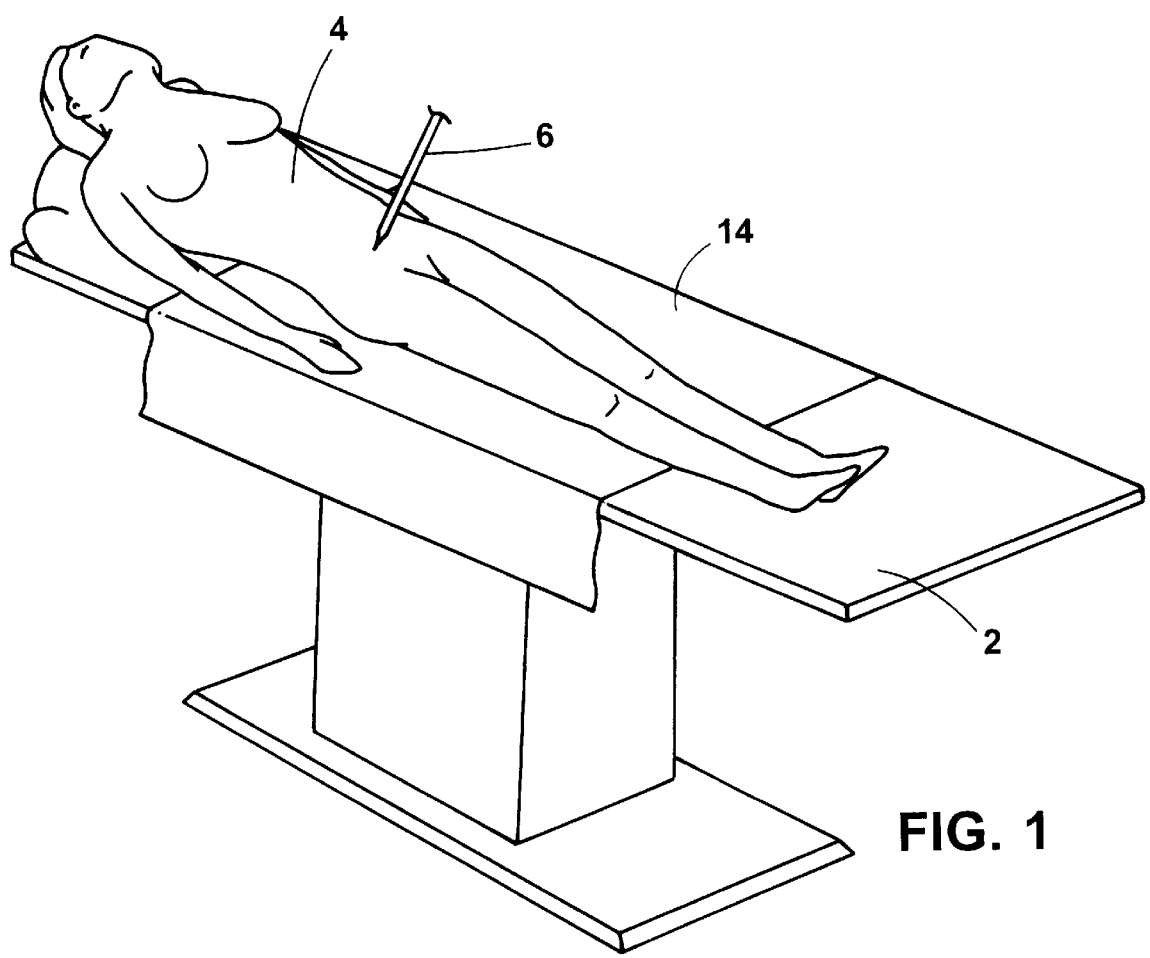
FIG. 1 is an illustration of a fluid collection drape according to the invention for use during surgery.
Figure 2:
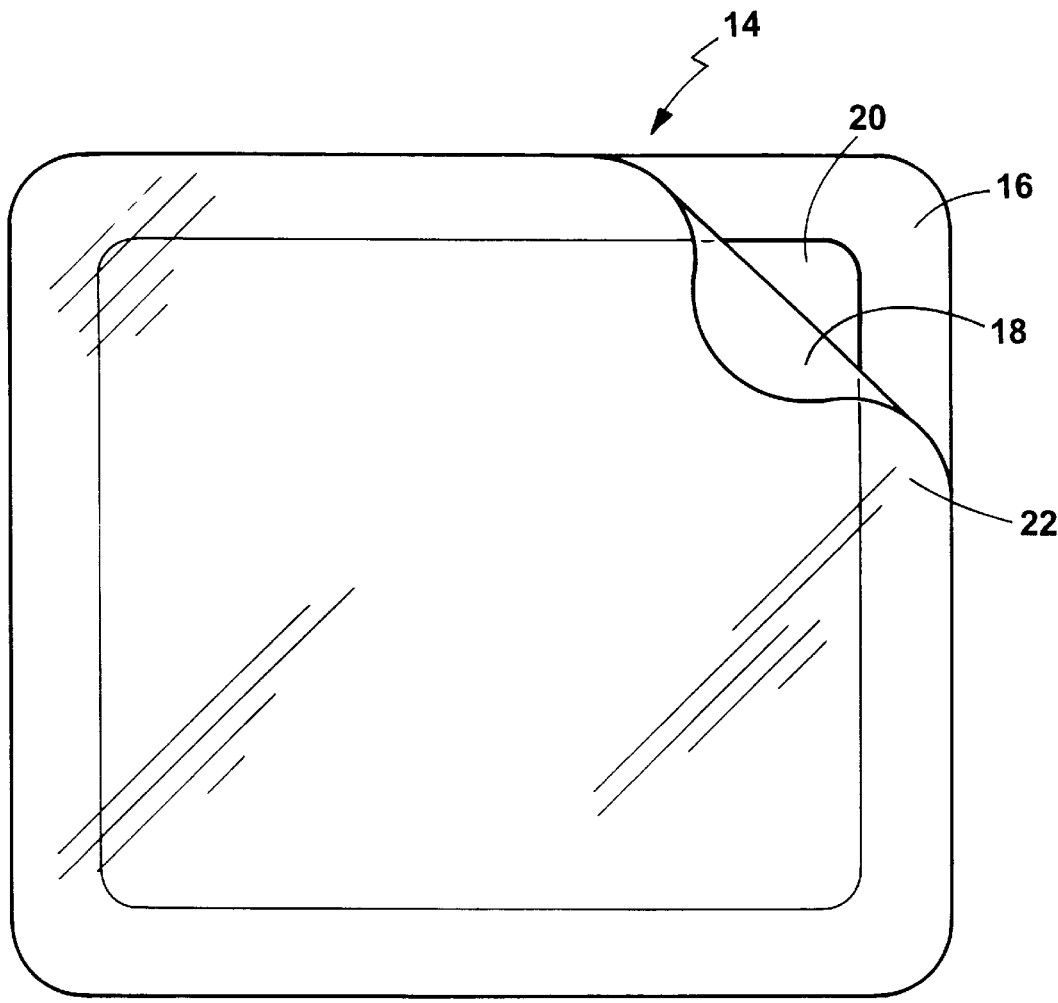
FIG. 2 shows the fluid collection drape of FIG. 1.

Referring to FIGS. 1 and 2, a fluid collection drape 14 for collecting fluid during surgery, for example, during ultrasonically assisted lipoplasty (UAL) with an ultrasonic probe 6, is shown. During UAL, fluid collection drape 14 is placed on a surgical operating table 2 of the kind normally found in a health care facility operating suite or treatment room, within the sterile field, under a patient 4. Fluid collection drape 14 includes a liner 16, a facing 18, and a substrate 20 sandwiched between liner 16 and facing 18. When in use, with fluid collection drape 14 positioned beneath the patient, liner 16 is in contact with the surgical table and facing 18 is oriented toward the patient.

Facing 18 is formed from a permeable material, such as spunbond non-woven polypropylene. Fluids flow through facing 18 to substrate 20, which absorbs the fluids. Liner 16 is formed from an impermeable material, such as polypropylene, such that fluids remain within the confines of substrate 20.

Substrate 20 is formed from two layers of paper, six ply per layer, and includes a highly absorbent material, such as a super absorbent polymer available from Kendall Healthcare Products of Mansfield, Mass., commonly used for diapers. The super absorbent polymer is generally concentrated toward the center of substrate 20, though it need not be. For example, the super absorbent polymer can be uniformly distributed in substrate 20. Fluid collection drape 14 absorbs more than, e.g., about 500 cc of fluid, preferably greater than about 100 cc of fluid per square foot.

Fluid collection drape 14 is sized to substantially cover the width of surgical operating table 2. Drape 14 covers a large is enough area beneath the patient such that fluid seeping from the incision sites is absorbed into fluid collection drape 14.

Figure 3:
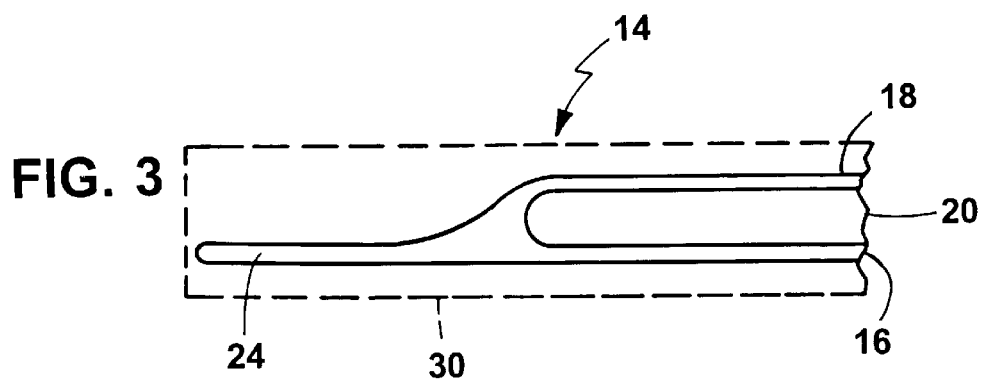
FIG. 3 shows a cross section of the fluid collection drape.

Fluid collection drape 14 is rectangularly shaped, with both liner 16 and facing 18 being, e.g., about 3.0 feet by 2.5 feet. Substrate 20 is about 33 inches by 27 inches. The thickness of substrate 20 is about 0.05 inches. Substrate 20 is smaller in overall area than lining 16 and facing 18 so that the edges of lining 16 and facing 18 overhang substrate 20 and form a perimeter 22 along the edge of drape 14. The width of perimeter 22 is about 1.5 inches. Referring to FIG. 3, liner 16 and facing 18 are attached to one another along perimeter 22 of drape 14, e.g., by a hot melt adhesive.

Fluid collection drape 14 is sterilized to eliminate bacteria and reduce the possibility of producing a biohazardous environment Sterilization is carried out, e.g., using gamma radiation, ethylene oxide, steam sterilization, or dry heat. The preferred technique is gamma radiation. The sterilization parameters should not be too high causing drape 14 to decompose, but should be high enough to sterilize drape 14. After fluid collection drape 14 is sterilized, drape 14 is placed in a peel pack 30 to maintain sterility until opened for use during surgery.

Other embodiments are within the scope of the following claims. For example, fluid collection drape 14 can be made in various sizes and shapes, as required by the procedure. The amount of absorbent material can be increased. Fluid collection drapes can be used to collect fluid during ultrasonic and non-ultrasonic liposuction procedures, as well as other aspiration procedures.

What is claimed is:

1. A fluid collection drape for use during surgery, comprising:

an impermeable liner;

a permeable facing; and a substrate sandwiched between the impermeable liner and the permeable facing, the substrate being configured to absorb at least about 100 cc of fluid per square foot so as to be capable of absorbing relatively large amounts of fluid that are released from a patient during the surgery;

the fluid collection drape being provided in a sterile condition and sized to substantially cover a width of a surgical operating table.

2. The fluid collection drape of claim 1, further comprising:

a package for storing the fluid collection drape in a sterile state.

3. The fluid collection drape of claim 1 wherein said fluid collection drape is constructed to be sterilizable by application of gamma radiation, ethylene oxide, steam or dry heat.

4. The fluid collection drape of claim 1 wherein the substrate is configured to absorb greater than about 500 cc of a fluid.

5. The fluid collection drape of claim 1, wherein the permeable facing is attached to the impermeable liner along a perimeter of the permeable facing and a perimeter of the impermeable liner.

6. The fluid collection drape of claim 5, wherein the permeable facing is attached to the impermeable lining by a hot melt adhesive.

7. The fluid collection drape of claim 1, wherein the fluid collection drape is about 3.0 feet by 2.5 feet.

8. The fluid collection drape of claim 1, wherein the substrate has a thickness of about 0.05 inches.

9. The fluid collection drape of claim 1, wherein the permeable facing comprises a spunbond non-woven polypropylene.

10. The fluid collection drape of claim 1, wherein the impermeable liner comprises a polypropylene.

11. The fluid collection drape of claim 1, wherein the substrate comprises a super absorbent polymer.

12. A method of defining a sterile operating environment during lipoplasty, comprising;

placing a sterile drape on an operating table, the sterile drape including a highly absorbent material capable of absorbing at least about 100 cc of fluid per square foot, performing lipoplasty on a patient so that relatively large amounts of fluid are released from the patient, and absorbing the fluid with the sterile drape during the lipoplasty.

13. The method of claim 12 wherein the surgery is lipoplasty.

14. The method of claim 13 wherein the surgery is ultrasonically assisted lipoplasty.

15. The method of claim 12 wherein placing the sterile drape includes placing the sterile drape under a patient.

16. A method of defining a sterile operating environment during surgery, comprising;

placing a sterile drape on an operating table under a patient, the sterile drape including an impermeable liner, a permeable facing, and a substrate sandwiched between the impermeable liner and the permeable facing, the sterile drape being placed with the permeable facing facing the patient, performing surgery on the patient so that relatively large amounts of fluid are released from the patient, and absorbing the fluid with the sterile drape.

17. The method of claim 16 wherein the step of absorbing includes absorbing greater than about 500 cc of fluid.

18. A fluid collection drape for use during surgery, comprising:

an impermeable liner;

a permeable facing; and a substrate sandwiched between interior portions of the impermeable liner and the permeable facing, peripheral portions of the permeable facing and the impermeable liner being directly attached together, the fluid collection drape being provided in a sterile condition and sized to substantially cover a width of a surgical operating table.

* * * * *

UNITED STATES PATENT AND TRADEMARK OFFICE
CERTIFICATE OF CORRECTION

PATENT NO. : 5,947,122
DATED : September 7, 1999
INVENTOR(S) : David McDonald et al.

It is certified that error appears in the above-identified patent and that said Letters Patent is hereby corrected as shown below:

On the title page: Item [56] in the "U.S. Patent Documents" section, add the reference --3,930,497  1/1976  Krebs--.

in the "References Cited" section, add the following:

"The Underlying Reason Our Pad is Best, Paper-Pak introduces the Ultima Supersorb™ Underpad", PAPER-PAK PRODUCTS, INC. (5 pages.

"Kimberly-Clark Medical Fabrics, New Product Bulletin 5.30 - Technological breakthrough for surgical drapes and covers", KIMBERLY-CLARK NONWOVEN FABRICS BUSINESS, 1995 (2 pages).

"Depend Absorbent Products - America's Leading Retail Brand", Depend®, 32-33, (2 pages).--

Col. 2, line 50, after replace "environment" with --enviromment.--

Signed and Sealed this

Twentieth Day of February, 2001

Attest:

NICHOLAS P. GODICI

Attesting Officer

Acting Director of the United States Patent and Trademark Office